United States Patent [19]

Lohaus et al.

[11] 3,972,888

[45] Aug. 3, 1976

[54] PROCESS FOR THE PREPARATION OF 1-HYDROXY-PYRIDONES

[75] Inventors: Gerhard Lohaus, Kelkheim, Taunus; Walter Dittmar, Hofheim, Taunus, both of Germany

[73] Assignee: Hoechst Aktiengesellschaft, Frankfurt am Main, Germany

[22] Filed: Aug. 23, 1974

[21] Appl. No.: 499,988

Related U.S. Application Data

[63] Continuation-in-part of Ser. No. 343,102, March 20, 1973, abandoned.

[30] Foreign Application Priority Data

Mar. 25, 1972 Germany............................ 2214608

[52] U.S. Cl. .................... 260/297 Z; 260/294.8 R; 260/294.9; 260/240 D; 260/240 E; 260/240 K; 260/240.9

[51] Int. Cl.² ...................................... C07D 213/50

[58] Field of Search .......... 260/297 Z, 240, 294.8 R

[56] References Cited

OTHER PUBLICATIONS

Wiley et al. "J. Am. Chem. Soc." vol. 78 pp. 2393–2398 (1956).

El—Kholy et al. "J. Chem Soc." (1961) pp. 4490–4498.

*Primary Examiner*—Henry R. Jiles
*Assistant Examiner*—Robert T. Bond
*Attorney, Agent, or Firm*—Curtis, Morris & Safford

[57] ABSTRACT

Method for making 6-substituted-1-hydroxy-2-pyridones, which may also be substituted in one or more of the 3-, 4-, and 5-positions, by reaction of the corresponding 2-pyrone with hydroxylamine or its salts in the presence of imidazole or a 2-aminopyridine which may be mono- or di-methyl substituted.

1 Claim, No Drawings

PROCESS FOR THE PREPARATION OF 1-HYDROXY-PYRIDONES

This is a continuation-in-part of our co-pending application Ser. No. 343,102 filed Mar. 20, 1973, now abandoned.

The present invention relates to a process for the preparation of 1-hydroxy-2-pyridones of the general formula

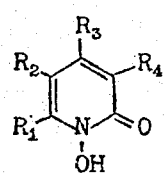

in which $R_1$ represents an alkyl radical of 1 to 17 carbon atoms which may be branched, an alkenyl radical of 2 to 17 carbon atoms, a cycloalkyl radical of 3 to 8 carbon atoms, a cyclohexylalkyl radical, a phenyl, phenylalkyl, benzhydryl, phenoxymethyl, phenylmercaptomethyl or phenyl-sulfonyl-methyl radical which may be substituted in the aromatic nucleus by one or several alkyl, alkoxy, amino, nitro, alkoxycarbonyl, cyano groups or halogen atoms, or a furyl or furylalkenyl radical, $R_2$ represents hydrogen or a lower alkyl, alkenyl or alkinyl radical or the benzyl group, $R_3$ represents hydrogen or a lower alkyl radical or the phenyl group, $R_4$ represents hydrogen or a lower alkyl, alkenyl radical, a methoxymethyl or the benzyl radical, or a chlorine or bromine atom, by the reaction of 2-pyrones of the general formula

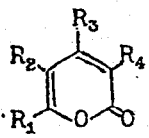

in which $R_1$, $R_2$, $R_3$ and $R_4$ have the meanings given above, with hydroxylamine or its salts in the presence of amines, characterized by working at room temperature to 150°C and using hydroxylamine in an amount up to 10 molar equivalents referred to 2-pyrone and using as amines imidazole or 2-aminopyridines which may be substituted by one or two methyl groups, the amines being used in a 20 fold molar quantity referred to the hydroxylamine or its salts.

In general, it is preferred to use as alkyl radical represented by $R_2$ to $R_4$, lower alkyl radicals containing 1 to 4 carbon atoms, in particular 1 or 2 carbon atoms, and as alkenyl radicals those which contain 2, 3 or 4 carbon atoms. The radicals which contain the phenyl nucleus are preferably those in which the phenyl nucleus is not substituted or substituted only once or twice, and among the phenalkyl groups, it is preferred to use the benzyl group.

It is known that the representatives of this general type have a good antibacterial and antimycotic activity (U.S. Pat. Nos. 2,540,213, 3,269,904, Belgian Pat. No. 738 288).

In some cases, the transformation of 2-pyrones into 1-hydroxy-2-pyridones by treatment with hydroxylamine-hydrochloride in pyridine has been described (J.Am. Chem.Soc. 78, 2393 (1956), J.Chem.Soc. [London] 1961, 4490). However, this process is limited to certain substituents at the α-pyrone ring and can, therefore, not be generalized. The attempt to apply this process to α-pyrones which carry substituents of a different nature will always result in the finding that the hydroxy-pyridones are obtained in a small yield and that their manufacture is practically not feasible according to this method.

Now, we have found that, surprisingly, 2-pyrones can be transformed in a generizable process, with good yields and under mild conditions, into 1-hydroxy-2-pyridones of high purity, by reacting them with hydroxylamine or its salts in the presence of 2-, 3- or 4-aminopyridine or imidazole or aminopyridine which is substituted at the nucleus or at the amino group by lower alkyl radicals. For example, by heating 4-methyl-6-cyclohexyl-2-pyrone with hydroxylamine in pyridine for 8 hours to 80°C., the corresponding 1-hydroxy pyridone is obtained in a yield of 2.6%. of the theory. When using α-picoline instead of pyridine, the yield is 3.0 %. When pyridine is replaced by the amines of the invention, operating under otherwise equal reaction conditions, the yields of the desired reaction product are about 20 times higher, for example with 2-aminopyridine 49 %, with 2-amino-6-methylpyridine 47 %, with 2-amino-4-methylpyridine 53 %, and with imidazole 47 % of theory. Moreover, the product prepared according to the process of the invention shows a particularly high degree of purity. These conditions are similar also with other α-pyrones.

As amines to be used within the scope of the invention, there may be mentioned: 2-aminopyridine, 2-amino-4-methylpyridine, 2-amino-6-methylpyridine, 2-amino-4,6-dimethylpyridine, 3-amino-6-methylpyridine, imidazole. In general, it is preferred to use the basic structures or the representatives of these two heterocycles which are substituted by a methyl group, in particular because they are technically easily accessible, they have a low molecular weight and a high dissolving power for the reaction partners and this not only for the organic components but also for the salts of hydroxylamine. Since most of these compounds are solid at room temperature, it may be of advantage to use liquid mixtures of these compounds if the reaction is to be carried out at low temperatures, for example at 20° C.

The reaction can be carried out within wide temperature limits, for example between room temperature and 150° C and more. In most cases satisfactory reaction speed are attained at temperatures in the range of from about 50° C to 120° C, which is, accordingly, the preferred temperature range.

The use of solvents or diluents which are inert under the reaction conditions is possible, but in general not necessary. However, in special cases it may be of advantage. Such solvents or diluents may be polar or non-polar, they may be miscible or immiscible with water. There may be used, for example, water, lower alcohols such as methanol, ethanol, isopropanol, ethylene glycol, ethylene glycol monomethyl ether, propylene glycol, amines such as triethylamine, morpholine, pyrrolidine, piperidine, pyridine, picoline, acid amides such as formamide, dimethylformamide, diethylformamide, monomethylacetamide, N-methylpyrrolidine, hexamethyl-phosphoric acid-triamide, esters such as ethyl acetate, methyl propionate, ethylene carbonate, ethers such as diethyl ether, di-isopropyl ether, dioxane, tetrahydrofurane, hydrocarbons such as methylene chloride, chlorobenzene, nitro compounds such as nitromethane, 2-nitropropane, nitrobenzene, nitriles such as acetonitrile, propionitrile, benzonitrile, furthermore compounds such as dimethyl sulfoxide, tetramethylenesulfone, etc.

The amine to be used according to the invention is suitably used in an at least equimolar quantity, referred to the hydroxyl-amine salt. Though it is possible to replace a part of it by other acid acceptors of organic or inorganic nature, this sometimes considerably reduces the reaction speed and the recovery of the amine, which is generally easy to carry out, for example by distillation or extraction, may be made difficult by such additions. On the other hand, the use of a large excess of the aminopyridine or imidazole, for example in a 20-fold molar quantity, referred to the hydroxylamine salt, does not affect the course of the reaction.

Of course, the hydroxylamine or its salts must be used in equimolar quantities, referred to the 2-pyrone to be reacted, but in order to accelerate the reaction and to increase the yields, it may also be used in excess, for example in quantities of up to 5 or 10 moles, referred to 1 mole of the pyrone used. It may also be of advantage to add the hydroxylamine in several portions during the reaction.

Compounds which can be obtained according to the process of the invention are, for example:

1-hydroxy-6-methyl-2-pyridone
1-hydroxy-4,6-dimethyl-pyridone
1-hydroxy-3,4,6-trimethyl-2-pyridone
1-hydroxy-4,5,6-trimethyl-2-pyridone
1-hydroxy-4-methyl-6-ethyl-2-pyridone
1-hydroxy-4-methyl-6-isopropyl-2-pyridone
1-hydroxy-4-methyl- 6-heptyl-2-pyridone
1-hydroxy- 3,4-dimethyl-6-isooctyl-2-pyridone
1-hydroxy-4-methyl-6-undecyl-2-pyridone
1-hydroxy-3,4-dimethyl-6-heptadecyl-2-pyridone
1-hydroxy-4-ethyl-5,6-dimethyl-2-pyridone
1-hydroxy-4,5-trimethylene-6-methyl-2-pyridone
1-hydroxy-4-methyl-6-cyclohexyl-2-pyridone
1-hydroxy-4-methyl-6-cyclohexylmethyl-2-pyridone
1-hydroxy-4-methyl-6-cyclohexylethyl-2-pyridone
1-hydroxy-4-methyl-6-isobutenyl-2-pyridone
1-hydroxy-4,6-dimethyl-5-benzyl-2-pyridone
1-hydroxy-3-benzyl-4,6-dimethyl-2-pyridone
1-hydroxy-4-methyl-6-benzyl-2-pyridone
1-hydroxy-4-methyl-6-(4-chlorobenzyl)-2-pyridone
1-hydroxy-6-phenyl-sulfonylmethyl-2-pyridone
1-hydroxy-3,4-dimethyl-6-(4-chlorophenylsulfonylmethyl)-2-pyridone
1-hydroxy-3-bromo-4,6-dimethyl-2-pyridone
1-hydroxy-3-chloro-4-methyl-6-(4-bromobenzyl)-2-pyridone
1-hydroxy-3,4-dimethyl-6-(2,4-dimethylbenzyl)-2-pyridone
1-hydroxy-4-methyl-6-benzhydryl-2-pyridone
1-hydroxy-4-methyl-6-(4-clorophenoxymethyl)-2-pyridone
1-hydroxy-4-methyl-6-(2,4,6-trichlorophenoxymethyl)-2-pyridone
1-hydroxy-4-methyl-6-(3-nitrophenoxymethyl)-2-pyridone
1-hydroxy-4-methyl-6-(phenylmercaptomethyl)-2-pyridone
1-hydroxy-4-methyl-6-phenyl-2-pyridone
1-hydroxy-4-methyl-6-(4-tolyl)-2-pyridone
1-hydroxy-3,4-dimethyl-6-(4-tolyl)-2-pyridone
1-hydroxy-4-methyl-6-(2,4-dimethylphenyl)-2-pyridone
1-hydroxy-4-methyl-6-(4-chlorophenyl)-2-pyridone
1-hydroxy-3,5,6-trimethyl-4-ethyl-2-pyridone
1-hydroxy-4-methyl-6-methylcyclohexyl-2-pyridone
1-hydroxy-4-methyl-6-bi-cycloheptyl-2-pyridone
1-hydroxy-4-methyl-5-ethyl-6-(4-tolyl)-2-pyridone
1-hydroxy-4,6-diphenyl-2-pyridone
1-hydroxy-4-phenyl-6-methyl-2-pyridone
1-hydroxy-3-ethyl-4-methyl-6-(4-tolyl)-2-pyridone
1-hydroxy-4-methyl-6-(4-nitrophenyl)-2-pyridone
1-hydroxy-4-methyl-6-(4-methoxyphenyl)-2-pyridone
1-hydroxy-4-methyl-6-phenyl-5,2'-(2-methylethylene)-2-pyridone
1-hydroxy-4-methyl-6-(4-cyanophenoxymethyl)-2-pyridone
1-hydroxy-4-methyl-6-(2-methoxycarbonylphenylmethyl)-2-pyridone
1-hydroxy-4-methyl-6-furyl-2-pyridone
1-hydroxy-4-methyl-6-(2-furyl-vinyl)-2-pyridone
1-hydroxy-4-methyl-6-styryl-2-pyridone
1-hydroxy-4-methyl-6-(4-dimethylaminostyryl)-2-pyridone
1-hydroxy-4-methyl-6-(4-phenyl-butadienyl)-2-pyridone
1-hydroxy-3-methoxymethyl-4-methyl-6-(4-tolyl)-2-pyridone
1-hydroxy-3-allyl-4-methyl-6-phenyl-2-pyridone
1-hydroxy-4-methyl-5-allyl-6-phenyl-2-pyridone
1-hydroxy-4-methyl-5-propargyl-6-phenyl-2-pyridone
1-hydroxy-4,6-diphenyl-2-pyridone.

This list of hydroxy-pyridones which can be prepared according to the invention is intended to illustrate the huge scope of the process of the invention. It is, of course, not limited to the compounds mentioned individually.

The α-pyrones used as starting products are easily accessible by known processes (for example, R. C. Elderfield, Heterocyclic compounds, 2nd Edition, Vol. 1, pages 354 et seq., J. Wiley and Sons Inc., New York 1959; Chemische Berichte 100, 658 (1967)).

The following Examples illustrate the invention:

EXAMPLE 1

2 g of 4-methyl-6-cyclohexyl-2-pyrone were heated with 1 g of hydroxylamine hydrochloride and 5 g of 2-aminopyridine to 80° C for 8 hours. The reaction mixture was then dissolved in methylene chloride, the amine was removed by shaking with dilute hydrochloric acid, the reaction product was extracted from the organic phase by means of dilute sodium hydroxide solution and the alkaline solution was acidified with acetic acid to a pH-valve of 6. The 1-hydroxy-4-methyl-6-cyclohexyl-2pyridone precipitated in crystalline form. It was filtered off with suction, washed with water and dried.

The yield was 1.05 g (49 % of the theory); melting point 143° C (Calc.: 6.8 % N, found: 6.8 % N).

When using, under otherwise equal reaction conditions, 2-amino-4-methylpyridine, there was obtained 1.15 g (53%), with 2-amino-6-methyl-pyridine 1.01 g (47 %), with 3-aminopyridine 0.52 g (24 %), with imidazole 1.01 g (47 %), with pyridine on the other hand 0.056 g (2.6 %) and with α-picoline 0.065 g (3.0 %).

EXAMPLE 2

2 g of 3-benzyl-4,6-dimethyl-2-pyrone, 6 g of 2-aminopyridine and 1 g of hydroxylamine-hydrochloride were heated for 8 hours to 70° C. After working up as described in Example 1, 0.65 g (30%) of 1-hydroxy-3-benzyl-4,6-dimethyl-2-pyridone were obtained; melting point 148° C (Calc.: 6.1 % N, found 6.1 % N).

When using pyridine instead of the amino-pyridine under otherwise equal reaction conditions, no hydroxy-pyridone was obtained.

EXAMPLE 3

2 g of 4-methyl-6-benzyl-2-pyrone, 6 g of 2-aminopyridine and 1 g of hydroxylamine hydrochloride were heated for 5 hours at 80° C. After the usual working up 1.41 g (66%) of 1-hydroxy-4-methyl-6-benzyl-2-pyridone melting at 135° C (calc.: 6.5 % N, found: 6.6 % N) were isolated.

When the aminopyridine is replaced by imidazole under otherwise equal reaction conditions, the yield was 1.33 g (62%), with pyridine on the other hand only 0.26 g (12%). In addition, the products obtained with aminopyridine and imidazole were pure white, whereas the product obtained with pyridine showed a yellow coloration.

EXAMPLE 4 a. 2 g of 4,6-dimethyl-5-benzyl-2-pyrone, 4 g of 2-aminopyridine and 0.9 g of hydroxylamine hydrochloride were heated for 5 hours to 80° C. After the usual working up, there were obtained 0.89 g (42 %) of 1-hydroxy-4,6-dimethyl-5-benzyl-2-pyridone melting at 165° C (Calc.: 6.1 % N, found: 6.1 % N).

Under similar conditions, there were obtained:

b. from 4-methyl-6-phenylsulfonylmethyl-2-pyrone, 1-hydroxy-4-methyl-6-phenylsulfonylmethyl-2-pyridone melting at about 260° C (36%; Calc.: 5.0 % N, found: 5.1 % N), c. from 4-ethyl-5,6-dimethyl-2-pyrone, 1-hydroxy-4-ethyl-5,6-dimethyl-2-pyridone melting at 139° C (33 %; Calc.: 8,4% N, found: 8.2 % N), d. from 3-bromo-4,6-dimethyl-2-pyrone, 1-hydroxy-3-bromo-4,6-dimethyl-2-pyridone melting at 220° C (37 %; Calc. 6.4 % N, found: 6,3 % N), e. from 4-methyl-6-isobutenyl-2-pyrone, 1-hydroxy-4-methyl-6-isobutenyl-2-pyridone melting at 116° C (24 %; Calc.: 7.8 % N, found: 7.7 % N), f. from 3,4-dimethyl-6-(4-tolyl)-2-pyrone, 1-hydroxy-3,4-dimethyl-6-(4-tolyl)-2-pyridone melting at 125° C (41 %; Calc.: 6.1 N, found: 5.8 % N), g. from 4-methyl-5-ethyl-6-(4-tolyl)-2-pyrone, 1-hydroxy-4-methyl-5-ethyl-6-(4-tolyl)-2-pyridone melting at 180° C (49 %; Calc.: 5.8 % N, found: 5.8 % N), h. from 4-methyl-6-(4-chlorophenoxy-methyl)-2-pyrone, 1-hydroxy-4-methyl-6-(4-chlorophenoxymethyl)-2-pyridone melting at 161° C (37 %; Calc.: 5.3 % N, found: 5.6 % N), i. from 4-methyl-6-phenylmercaptomethyl-2-pyrone, 1-hydroxy-4-methyl-6-phenylmercaptomethyl-2-pyridone melting at 126° C (43 %; Calc.: 5.7 % N, found: 5.8 % N), k. from 4,6-dimethyl-2-pyrone, 1-hydroxy-4,6-dimethyl-2-pyridone melting at 135° C (46%; Calc. 10.0 % N, found: 10.1 % N), l. from 3,4,6-trimethyl-2-pyrone, 1-hydroxy-3,4,6-trimethyl-2-pyridone melting at 130° C (41 %; Calc.: 9.2 %N, found: 9.4 %), m. from 6-methyl-2-pyrone, 1-hydroxy-6-methyl-2-pyridone melting at 141° C (34 %; Calc.: 11.2 % N, found: 11.0 % N), n. from 4-methyl-6-heptyl-2pyrone, 1-hydroxy-4-methyl-6-heptyl-2-pyridone melting at 48° C (38 %; Calc.: 6.3 %N, found: 6.0% N), o. from 4-methyl-6-undecyl-2-pyrone, 1-hydroxy-4-methyl-6-undecyl-2-pyridone melting at 63° C (33 %; Calc.: 5.0 % N, found: 5.4 % N), p. from 4,5-trimethylene-6-methyl-2-pyrone, 1-hydroxy-4,5-trimethylene-6-methyl-2-pyridone melting at 177° C (44 %; Calc.: 8.5 % N, found 8.4 % N), q. from 4-methyl-6-(4-chlorophenyl)-2-pyrone, 1-hydroxy-4-methyl-6-(4-chlorophenyl)-2-pyridone melting at 123° C (26 %; Calc.: 6.0 % N, found 6.1 % N), r. from 4,6-diphenyl-2-pyrone, 1-hydroxy-4,6-diphenyl-2-pyridone melting at 160° C (91 %; Calc.0 5.3 % N, found: 5.3 % N), s. from 4-methyl-6-(α-furyl)-2-pyrone, 1-hydroxy-4-methyl-6-(α-furyl)-2-pyridone melting at 147° C (26 %; Calc.: 7.3 % N, found: 7.6 % N), t. from 4-methyl-6-[2-(α-furyl)-vinyl]-2-pyrone, 1-hydroxy-4-methyl-6-[2-(α-furyl)-vinyl]-2-pyridone melting at 166° C (28 %; Calc.: 6.5 N, found 6.4 % N), u. from 4-phenyl-6-methyl-2-pyrone, 1-hydroxy-4-phenyl-6-methyl-2-pyridone melting at 185° C (62 %; Calc.: 7.0 % N, found: 6.7 % N), v. from 4-methyl-6-styryl-2-pyrone, 1-hydroxy-4-methyl-6-styryl-2-pyridone melting at 176° C (34 %; Calc.: 6.2 % N, found: 6.0 % N), w. from 4-methyl-6-[4-phenyl-butadiene-(1)-yl]-2-pyrone, 1-hydroxy-4-methyl-6-[4-phenyl-butadiene-(1)-yl]-2-pyridone melting at 220° C (49 %; Calc.: 5.5 % N, found 5.5 % N), x. from 4-methyl-6-(4-nitrophenyl)-2-pyrone, 1-hydroxy-4-methyl-6-(4-nitrophenyl)-2-pyridone melting at 190° C (18 %; Calc.: 11.4 %, found: 10.9 % N).

EXAMPLE 5

1 g of 4-methyl-6-(4-tolyl)-2-pyrone, 0.6 g of hydroxylamine hydrochloride and 4 g of 2-aminopyridine were heated for 1 hour to 80° C. After the usual working up, 0.173 g (16.1 %) of 1-hydroxy-4-methyl-6-(4-tolyl)-2-pyridone melting at 125° C (calc.: 6.5 % N, found: 6,6 % N) were isolated. When using pyridine instead of aminopyridine under otherwise equal reaction conditions, the yield was 0.012 g (1.1 %) only.

Under the same conditions, 1-hydroxy-4-methyl-6-phenyl-2-pyridone melting at 135° C (Calc.: 7.0 % N, found 7.0 % N) was obtained from 4-methyl-6-phenyl-2-pyrone with 2-aminopyridine in a yield of 17.2 %, but with pyridine in a yield of only 1.3 %.

EXAMPLE 6

1 g of 4-methyl-6-(4-dimethylaminostyryl)-2-pyrone, 3g of 2-aminopyridine and 0.4 g of hydroxylamine hydrochloride were heated for 10 hours to 70° C and the reaction product was then precipitated by the addition of water. Melting point: about 250° C, 0.91 g (86 %; Calc.: 10.4 % N, found: 10.0 % N).

EXAMPLE 7

The process was carried out as described in Example 4, but using 2-amino-6-methyl-pyrimidine instead of 2-aminopyridine. There were obtained:

a. from 4-methyl-6-cyclohexylmethyl-2-pyrone, 1-hydroxy-4-methyl-6-cyclohexylmethyl-2-pyridone melting at 131° C (44 %; Calc.: 6.3 % N, found: 6.5 % N), b. from 4-methyl-6-isopropyl-2-pyrone, 1-hydroxy-4-methyl-6-isopropyl-2-pyridone melting at 110° C (47 %; Calc.: 8.4 % N, found: 8.2 % N), c. from 4-methyl-6-(4-methoxyphenyl)-2-pyrone 1-hydroxy-4-methyl-6-(4-methoxyphenyl)-2-pyridone melting at 174° C (23 %; Calc.: 6.1 % N, found: 5.9 % N), d. from 4-methyl-6-phenyl-5,2'-(2-methylethylene)-2-pyrone, 1-hydroxy-4-methyl-6-phenyl-5,2'-(2-methylethylene)-2-pyridone melting at 174° C (26 %; Calc.: 5.8 % N, found: 5.6 % N), e. from 4-methyl-6-(3-nitrophenoxymethyl)-2-pyrone, 1-hydroxy-4-methyl-6-(3-nitrophenoxymethyl)-2-pyridone melting at 216° C (34 %; Calc.: 10.2 % N, found: 10.0 % N), f. from 4-methyl-6-ethyl-2-pyrone, 1-hydroxy-4-methyl-6-ethyl-2-pyridone melting at 110° C (41 %; Calc.: 9.2 % N, found: 9.4 % N), g. from 3-ethyl-4-methyl-6-(4-tolyl)-2-pyrone, 1-hydroxy-3-ethyl-4-methyl-6-(4-tolyl)-2-pyridone melting at 100° C (29 %; Calc.: 5.8 % N, found: 5.5 % N), h. from 3-methoxymethyl-4-methyl-6-(4-tolyl)-2-pyrone, 1-hydroxy-3-methoxymethyl-4-methyl-6-(4-tolyl)-2-pyridone melting at 130° C (51%; Calc.: 5.4 % N, found: 5.4 % N), i. from 4-methyl-6-($\beta$-cyclohexylethyl)-2-pyrone, 1-hydroxy-4-methyl-6-($\beta$-cyclohexylethyl)-2-pyridone melting at 90° C (41 %; Calc.: 6.0 % N, found: 5.8 % N), k. from 4-methyl-6-benzhydryl-2-pyrone, 1-hydroxy-4-methyl-6-benzhydryl-2-pyridone melting at 191° C (33 %; Calc.: 4.7 % N, found: 4.7 % N), l. from 4-methyl-6-(2-Chlorobenzyl)-2-pyrone, 1-hydroxy-4-methyl-6-(2-chlorobenzyl)-2-pyridone; M.p. 122°C (68 %, calc. 5.6 % N, found 5.7 % N)

m. from 4-methyl-6-(3-heptyl)-2-pyrone; 1-hydroxy-4-methyl-6-(3-heptyl)-2-pyridone in a form of a viscous oil (61 %, calc. 6.3 % N, found 6.1 % N)

n. from 4-methyl-6-[2-(1-naphthyl)-vinyl]-2-pyrone; 1-hydroxy-4-methyl-6-[2-(1-naphthyl)-vinyl]-2-pyridone; M.p. 196°C (54 %, calc. 5.1 % N, found 5.2 N)

o. from 4-methyl-6-(4-phenylbutyl)-2-pyrone; 1-hydroxy-4-methyl-6-(4-phenylbutyl)-2-pyridone M.p. 73°C (64 %, calc. 5.5 % N, found 5.4 % N)

p. from 3-butyl-4,6-dimethyl-2-pyrone; 1-hydroxy-3-butyl-4,6 dimethyl-2-pyridone; M.p. 76°C (60 %, calc. 7.2 % N, found 7.3 % N)

q. from 5-butyl-4,6-dimethyl-2-pyrone; 1-hydroxy-5-butyl-4,6-dimethyl-2-pyridone; M.p. 133°C (47 %, calc. 7.2 % N, 7.5 % N)

r. from 4-methyl-6-heptadecyl-2-pyrone; 1-hydroxy-4-methyl-6-heptadecyl-2-pyridone, M.p. 60°C (42 %, calc. 3.9 % N, found 3.5 % N)

s. from 4-methyl-6-[2-(1-naphthyl)-ethyl]-2-pyrone; the 1-hydroxy-4-methyl-6-[2-(1-naphthyl)-ethyl]-2-pyridone; M.p. 159°C (54 %, calc. 5.0 % N, found 5.2 % N)

t. from 4-methyl-6-(2-phenylethyl)-2-pyridone; M.p. 124°C (58 %, calc. 6.1 % N, found 6.1 % N)

u. from 4-methyl-6-(1-phenylethyl)-2-pyrone; 1-hydroxy-4-methyl-6-(1-phenylethyl)-2-pyridone; M.p. 110°C (62 %, calc. 6.1 % N, found 6.3 % N)

v. from 4-methyl-6-bicycloheptyl-2-pyrone; 1-hydroxy-4-methyl-6-bicycloheptyl-2-pyridone; M.p. 147°C (55 %, calc. 6.4 % N, found 6.4 % N)

w. from 4-methyl-6-(4-tolylthio-methyl)-2-pyrone; 1-hydroxy-4-methyl-6-(4-tolylthio-methyl)-2-pyridone; M.p. 115°C (68 %, calc. 5.4 % N, found 5.5 % N)

x. from 4-methyl-6-(2-naphthyl)-2-pyrone; 1-hydroxy-4-methyl-6-(2-naphthyl)-2-pyridone, M.p. 205°C (24 %, calc. 5.6 % N, found 5.6 % N)

y. from 4-methyl-6-(2,4,6-trichlorophenoxy-methyl)-2-pyrone, 1-hydroxy-4-methyl-6-(2,4,6-trichlorophenoxy-methyl)-2-pyridone, M.p. 216°C (54 %, calc. 4.2 % N, found 4.1 % N)

z. from 4-methyl-6-(2,4-dimethyl-phenyl)-2-pyrone; 1-hydroxy-4-methyl-6-(2,4-dimethyl-phenyl)-2-pyridone; M.p. 109°C (23 %, calc. 6.1 % N, found 6.1 % N)

EXAMPLE 8 a. 1 g of 4-methyl-5-propargyl-6-phenyl-2-pyrone, 1.5 g of hydroxylamine hydrochloride and 3 g of 2-amino-4-methyl-pyridine were heated for 9 hours to 80° C. After the usual working up, there were obtained 0.82 g (77 %) of 1-hydroxy-4-methyl-5-propargyl-6-phenyl-2-pyridone melting at 200° C (Calc.: 5.9 % N, found: 5.8 % N).

Under similar conditions there were obtained:

b. from 3-allyl-4-methyl-6-phenyl-2-pyrone, 1-hydroxy-3-allyl-4-methyl-6-phenyl-2-pyridone melting at 115° C (60 %; Calc.: 5.8 % N, found: 5.7 % N), c. from 4-methyl-5-allyl-6-phenyl-2-pyrone, 1-hydroxy-4-methyl-5-allyl-6-phenyl-2-pyridone melting at 176° C (56 %; Calc.: 5.8 % N, found: 5.5 % N).

EXAMPLE 9

5 g of 4-methyl-6-(4-chlorobenzyl)-2-pyrone, 2.5 g of hydroxylamine hydrochloride and 10 g of 2-aminopyridine were heated for 16 hours to 60°C. After the usual working up, there were obtained 3.3 g (62 %) of 1-hyroxy-4-methyl-6-(4-chlorobenzyl)-2-pyridone melting at 142° C (Calc.: 5.6% N, found 5.9 % N).

EXAMPLE 10

10 g of 4-methyl-6-(2,4,4-trimethylpentyl)-2-pyrone, 5 g of hydroxylamine hydrochloride and 20 g of 2-aminopyridine were heated for 26 hours to 70°C, whereupon after 17 hours a further 2 g of hydroxylamine were added. Working up was effected as usual and there were obtained 7.1 g (67 %) of 1-hydroxy-4-methyl-6-(2,4,4-trimethylpentyl)-2-pyridone melting at 108° C (Calc.: 5.9 % N, found 5.9 % N).

EXAMPLE 11

2 g of 4-methyl-6-cyclohexyl-2-pyrone and 1 g of hydroxylamine were dissolved in a mixture of 1.5 g of 2-aminopyridine and 4.5 g of 2-amino-6-methylpyridine and stored for 9 days at room temperature. After the usual working up, there were obtained 0.79 g (37 %) of 1-hydroxy-4-methyl-6-cyclohexyl-2-pyridone melting at 143° C.

EXAMPLE 12

1 g of 3,4-dimethyl-6-(2,4-dimethylbenzyl)-2-pyrone, 0.5 g of hydroxylamine hydrochloride and 3 g of imidazole were heated for 8 hours to 75° C and then worked up in the usual manner. There were obtained 0.63 g (59 %) of 1-hydroxy-3,4-dimethyl-6-(2,4-dimethylbenzyl)-2-pyridone melting at 141° C (Calc.: 5.4 % N; found: 5.6 % N). When using pyridine instead of imidazole under otherwise equal reaction conditions, the yield was 0.003 g (0.3 %).

EXAMPLE 13

20 g of 4-methyl-6-cyclohexyl-2-pyrone, 8 g of hydroxylamine sulfate and 50 g of imidazole were heated to 90° C. Further 10 g of hydroxylamine sulfate were added portionwise in the course of 3 hours. After a reaction time of 5 hours, the mixture was worked up. 11.8 g of 1-hydroxy-4-methyl-6-cyclohexyl-2-pyridone melting at 143° C were obtained.

EXAMPLE 14

2 g of 4-methyl-6-cyclohexyl-2-pyrone, 1.2 g of hydroxylamine sulfate and 5 g of imidazole were heated for 1 hour to 110° C. The yield of 1-hydroxy-4-methyl-6-cyclohexyl-2-pyridone, melting up to 143° C, was 1.01 g.

When carrying out the reaction by heating for 15 minutes to 150° C, the yield was 0.94 g.

EXAMPLE 15

1 g of 4-methyl-6-cyclohexyl-2-pyrone, 0.5 g of hydroxylamine hydrochloride, 2 g of aminopyridine and 1 g of toluene were heated for 5 hours to 80° C. After about 1 hour, the system, which initially was a two-phase system, became homogeneous. The yield of hydroxy pyridone was 0.44 g. When adding 1 g of glycolmonomethyl ether instead of the toluene, the yield was 0.47 g.

EXAMPLE 16

1 g of 4,6-diphenyl-2-pyrone, 3 g of α-aminopyridine and 0,6 g of hydroxylamine hydrochloride were heated for 30 minutes to 70°C. The whole was dissolved in 50 ml of benzene and 50 ml of 2N hydrochloric acid and shaken. The organic phase was extracted with 40 ml of 0.5 N sodium hydroxide solution and the alkaline solution was adjusted to pH 6 by means of acetic acid. The product that had precipitated was filtered off with suction, washed with water and dried. The yield of colorless hydroxypyridone was 0.73 g (69 %), melting point 161°C.

When using 6-methyl-2-amino-pyridine instead of aminopyridine under otherwise equal conditions, 0.74 g (70 %) were obtained, with 4,6-dimetyl-2-aminopyridine 0.715 g (67 %), with imidazole 0.74 g (70 %). On the other hand, the yield with pyridine was only 0.04 g (3.8 %), with 2-methyl pyridine 0.035 g (3.4 %), with 2,4-dimethylpyridine 0.03 g (2.9 %), with triethylamine 0.07 g (6.6 %). Moreover the products obtained with the 4 last-mentioned amines were yellowish discolored. With N,N-dimethyl-2-aminopyridine instead of 2-aminopyridine, no reaction in the desired sense was obtained.

We claim:
1. The method of making a 1-hydroxy-2-pyridone of the formula

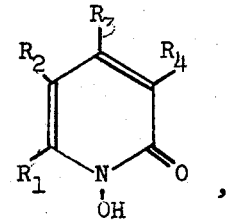

wherein $R_1$ is straight-chain or branched alkyl having 1 to 17 carbon atoms, alkenyl having 2 to 17 carbon atoms, cycloalkyl having 3 to 8 carbon atoms, cyclohexylalkyl having 1 to 2 carbon atoms in the alkyl, furyl, or furylvinyl, or is phenyl, phenylalkyl having 1 to 4 carbon atoms in the alkyl, phenylalkenyl having 2 to 4 carbon atoms in the alkenyl, benzhydryl, phenoxymethyl, phenylmercaptomethyl, or phenylsulfonylmethyl, all of which may be at least mono-substituted in the phenyl nucleus by methyl, methoxy, amino, nitro, methoxycarbonyl, cyano, or halogen, $R_2$ is hydrogen, lower alkyl, lower alkenyl, lower alkinyl, or benzyl;

$R_3$ is hydrogen, lower alkyl, or phenyl;

$R_4$ is hydrogen, lower alkyl, lower alkenyl, methoxymethyl, benzyl, chlorine, or bromine, which comprises reacting a 2-pyrone of the formula

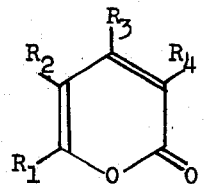

wherein $R_1$–$R_4$ have their earlier meanings, at a temperature from room temperature to 150°C., with from 1 to 10 mol equivalents, per mol of 2-pyrone, of hyroxylamine or a salt thereof in the presence of 1 to 20 mols, per mol of hydroxylamine or of hydroxylamine salt, of imidazole, a 2-aminopyridine, or of a mono- or dimethyl substituted 2-aminopyridine.

* * * * *